US012590962B2

(12) United States Patent
Hirahara et al.

(10) Patent No.: US 12,590,962 B2
(45) Date of Patent: Mar. 31, 2026

(54) METHOD FOR PREDICTING FORMATION OF THROMBUS OR RISK OF THROMBUS FORMATION IN MEDICAL DEVICE PERFORMING BLOOD CIRCULATION BY PUMP

(71) Applicant: TERUMO KABUSHIKI KAISHA, Shibuya-ku (JP)

(72) Inventors: Ichiro Hirahara, Ashigarakami-gun (JP); Shinpei Furukawa, Ashigarakami-gun (JP); Koko Kumano, Ashigarakami-gun (JP); Hideki Sato, Ashigarakami-gun (JP)

(73) Assignee: TERUMO KABUSHIKI KAISHA, Shibuya-ku (JP)

( * ) Notice: Subject to any disclaimer, the term of this patent is extended or adjusted under 35 U.S.C. 154(b) by 803 days.

(21) Appl. No.: 17/911,034

(22) PCT Filed: Mar. 2, 2021

(86) PCT No.: PCT/JP2021/007826
§ 371 (c)(1),
(2) Date: Sep. 12, 2022

(87) PCT Pub. No.: WO2021/182171
PCT Pub. Date: Sep. 16, 2021

(65) Prior Publication Data
US 2023/0160896 A1 May 25, 2023

(30) Foreign Application Priority Data
Mar. 13, 2020 (JP) ................................. 2020-044275

(51) Int. Cl.
*G01N 33/573* (2006.01)

(52) U.S. Cl.
CPC . *G01N 33/573* (2013.01); *G01N 2333/96486* (2013.01)

(58) Field of Classification Search
CPC ............ C12Q 1/6883; C12Q 2600/118; C12Q 2600/158; G01N 2333/96419;
(Continued)

(56) References Cited

U.S. PATENT DOCUMENTS 10,556,967 B2 2/2020 Miyakoshi et al.
2014/0141986 A1* 5/2014 Spetzler ................. G01N 33/50
435/7.1
2017/0246632 A1 8/2017 Slepian et al.

FOREIGN PATENT DOCUMENTS

JP 2012052944 A 3/2012
JP 2016059386 A 4/2016
(Continued)

OTHER PUBLICATIONS

Chen et al., "Device-Induced Platelet Dysfunction in Mechanically Assisted Circulation Increases the Risks of Thrombosis and Bleeding," Artificial Organs, Blackwell Scientific Publications, Inc., Boston, US, (Mar. 28, 2019), vol. 43, No. 8, pp. 745-755.
(Continued)

*Primary Examiner* — Jennifer Wecker
(74) *Attorney, Agent, or Firm* — BUCHANAN INGERSOLL & ROONEY PC

(57) ABSTRACT

Provided is a means capable of predicting a formation of thrombus or a risk thereof in a medical device performing blood circulation by a pump, by a simple and minimally invasive method. A method for predicting a formation of thrombus or a risk thereof in a medical device performing blood circulation by a pump, wherein it is predicted that thrombus is formed or there is a risk thereof in the medical device when a concentration or expression amount of (Continued)

ADAM28 in a body fluid sample collected from a subject wearing the medical device is elevated compared with a reference value.

4 Claims, 1 Drawing Sheet

(58) Field of Classification Search
CPC ..... G01N 2333/96486; G01N 2800/50; G01N 33/573; G01N 33/6893
See application file for complete search history.

(56) References Cited

FOREIGN PATENT DOCUMENTS

| | | | | |
|---|---|---|---|---|
| JP | 2017150966 A | | 8/2017 | |
| JP | 2020065632 A | * | 4/2020 | ............. B21D 22/28 |
| WO | 2020/054877 A1 | | 3/2020 | |

OTHER PUBLICATIONS

Zucker et al., "New Wrinkle Between Cancer and Blood Coagulation: Metastasis and Cleavage of von Willebrand Factor by ADAM28," Journal of the National Cancer Institute, (May 25, 2012), vol. 104, No. 12, pp. 887-888.

The extended European Search Report issued Nov. 28, 2022, by the European Patent Office in corresponding European Patent Application No. 21768232.7-1118. (8 pages).

"Extracorporeal Life Support Organization (ELSO) Guidelines for Adult Respiratory Failure", Aug. 2017, pp. 1-32, Version 1.4. (32 pages) (discussed in paragraph [0002] of the specification).

Brogan, Thomas V., et al., "Extracorporeal membrane oxygenation in adults with severe respiratory failure: a multi-center database", Intensive Care Med., published online Sep. 22, 2009, pp. 2105-2144, vol. 35, No. 12, Springer and ESICM. (10 pages) (discussed in paragraph [0003] of the specification).

Esper, Stephen A., et al., "Extracorporeal membrane oxygenation in the adult: a review of anticoagulation monitoring and transfusion", Anethesia & Analgesia, Apr. 2014, pp. 731-743, vol. 118, No. 4. (13 pages) (discussed in paragraph [0003] of the specification).

Extracorporeal Life Support Organization, "The Risks & Complications of ECMO/ECLS", ECMO & ECLS Risks: Extracorporeal Membrane Oxygenation, https://www.elso.org/Resources/RisksandComplications.aspx. (1 page) (discussed in paragraph [0003] of the specification).

Fitousis, Kalliopi, et al. "Evaluation of a pharmacy managed heparin protocol for extracorporeal membrane oxygenation patients", Perfusion, 2017 (month unknown), pp. 238-244, vol. 32, No. 3, Sage Publications Co., UK. (7 pages) (discussed in paragraph [0002] of the specification).

Horiuchi, Hisanori, et al., Acquired von Willebrand syndrome associated with intractable cardiovascular disease. (2 pages) (exact publication date unknown, but at least as early as Mar. 13, 2022) (discussed in paragraph [0004] of the specification).

Horiuchi, Hisanori, The acquired von Willebrand syndrome co-existing with cardiovascular diseases Study (The AVEC Study), Dec. 28, 2021. (2 pages) (discussed in paragraph [0005] of the specification).

International Search Report (PCT/ISA/210) with translation and Written Opinion (PCT/ISA/237) mailed on Apr. 6, 2021, by the Japanese Patent Office as the International Searching Authority for International Application No. PCT/JP2021/007826. (9 pages).

Mochizuki, Satsuki et al., "Effect of ADAM28 on Carcinoma Cell Metastasis by Cleavage of von Willebrand Factor", Journal of the National Cancer Institute, Jun. 20, 2012, pp. 906-922, vol. 104, Issue 12, Oxford University Press. (17 pages) (discussed in paragraph [0006] of the specification and cited in International Search Report).

Moynihan, Katie, et al., "Coagulation monitoring correlation with heparin dose in pediatric extracorporeal life support", Perfusion, 2017 (month unknown), pp. 675-685, vol. 32, No. 8, Sage Publications Co., UK. (11 pages) (discussed in paragraph [0002] of the specification).

Sakatsume, Ko, et al., "Acquired von Willebrand syndrome caused by high shear stress", Artificial Organs, 2016 (month unknown), pp. 225-228, vol. 45, No. 3. (4 pages) (discussed in paragraph [0004] of the specification).

Sakatsume, Ko, et al., "Intractable Bleeding Tendency Due to Acquired Von Willebrand Syndrome After Jarvik 2000 Implant", Journal of Artificial Organs, Mar. 16, 2016, pp. 289-292, vol. 9, Springer. (4 pages) (discussed in paragraph [0005] of the specification).

Sklar, Michael C., et al., "Anticoagulation Practices during Venovenous Extracorporeal Membrane Oxygenation for Respiratory Failure", Systematic Review, Ann Am Thorac Soc., Dec. 2016, pp. 2242-2250, vol. 13, No. 12, American Thoracic Society. (9 pages) (discussed in paragraph [0003] of the specification).

Ujiie, Yoshihito, Respiratory ECMO Manual, 2014 (month unknown), Kokuseido Co., Ltd., pp. 88-93. (3 pages) (discussed in paragraph [0002] of the specification).

Von Willebrand (ADAMTS13), 2009 (month unknown), pp. 1586-1592, vol. 98, No. 7. (7 pages) (discussed in paragraph [0005] of the specification).

Draper, Karen V., et al., "GI bleeding in patients with continuous-flow left ventricular assist devices: a systematic review and meta-analysis", Gastrointestinal Endoscopy, Mar. 24, 2014, pp. 435-446, vol. 80, No. 3, American Society for Gastrointestinal Endoscopy. (13 pages) (discussed in paragraph [0005] of the specification).

"Evaluation Methods of Next-Generation Assisted Circulation Systems" in Project to Promote the Practical Application of Innovative Pharmaceuticals, Medical Devices, and Regenerative Medical Products, Draft Evaluation Guidelines for Medium- and Long-Term Respiratory/Circulatory Assist (ECMO/PCPS) Systems, Mar. 2017. (30 pages) (discussed in paragraph [0002] of the specification).

Kalbhenn, Johannes, et al., "Early diagnosis of acquired von Willebrand Syndrome (AVWS) is elementary for clinical practice in patients treated with ECMO therapy", Journal of Atheroscler and Thrombosis, 2015 (month unknown), pp. 265-271, vol. 22, No. 3. (7 pages) (discussed in paragraph [0005] of the specification).

Ruggeri, Zaverio M., et al., "Variant von Willebrand's Disease: Characterization Of Two Subtypes By Analysis Of Multimeric Composition Of Factor VIII/Von Willebrand Factor In Plasma And Platelets", The Journal of Clinical Investigation, Jun. 1980, pp. 1318-1325, vol. 65, No. 6, The American Society for Clinical Investigation, Inc. (9 pages) (discussed in paragraph [0004] of the specification).

Office Action (Communication pursuant to Article 94(3) EPC) issued on Oct. 15, 2025, in corresponding European Patent Application No. 21768232.7. (6 pages).

* cited by examiner

[Fig. 1]
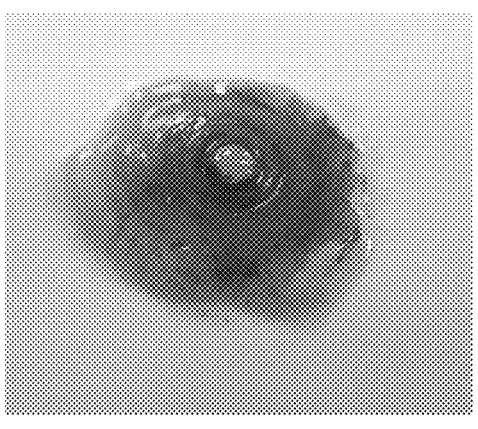
[Fig. 2]
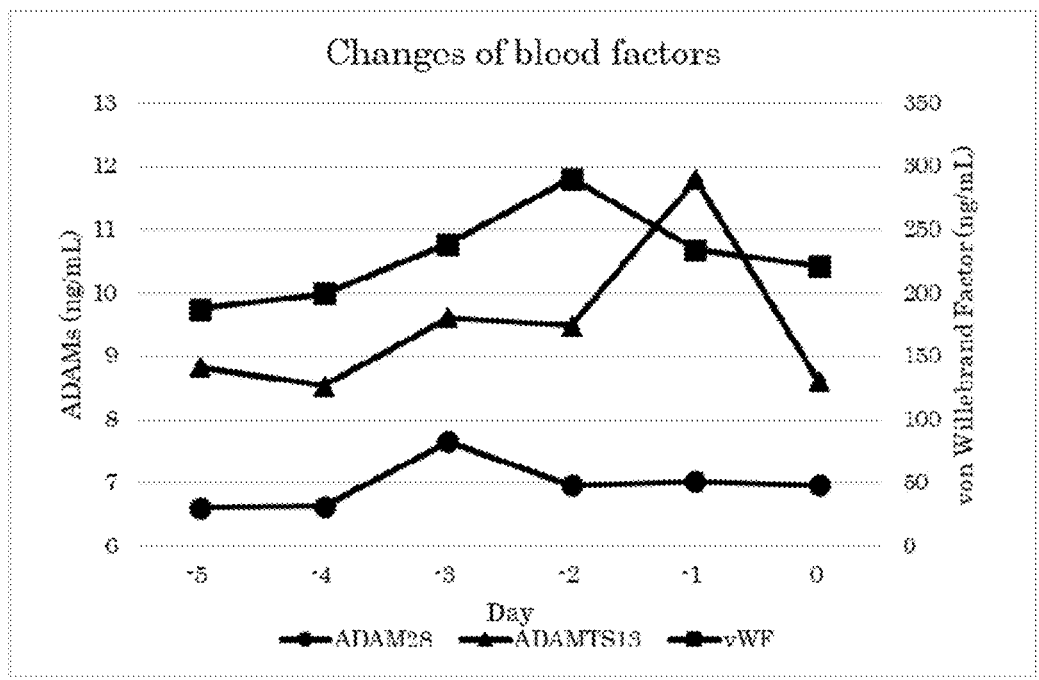

METHOD FOR PREDICTING FORMATION OF THROMBUS OR RISK OF THROMBUS FORMATION IN MEDICAL DEVICE PERFORMING BLOOD CIRCULATION BY PUMP

TECHNICAL FIELD

The present invention relates to a method for predicting a formation of thrombus or a risk thereof in a medical device performing blood circulation by a pump.

BACKGROUND ART

When life is difficult to sustain even with collective treatments due to respiratory failure, treatments with Extracorporeal Membrane Oxygenation (ECMO) and Percutaneous Cardiopulmonary Support (PCPS) are performed. ECMO/PCPS is a treatment that uses an artificial lung and a pump which serve as an alternative to the heart and the lung. The circuit (ECMO/PCPS system) is composed of parts such as an artificial lung, a blood pump, vascular deliveries, connecting tubes, and connectors (Working Group on "Evaluation Methods of Next-Generation Assisted Circulation Systems" in Project to Promote the Practical Application of Innovative Pharmaceuticals, Medical Devices, and Regenerative Medical Products. Draft Evaluation Guidelines for Medium- and Long-Term Respiratory/Circulatory Assist (ECMO/PCPS) Systems). The current ECMO/PCPS system uses essentially the same parts as those used in the cardiopulmonary artificial device for cardiotomy, and most of these parts are pharmaceutically approved for use within 6-hours in the assumption of normal cardiotomy. In normal cardiotomy, the cardiopulmonary artificial device performs a treatment of about several hours under a strong anticoagulant therapy by systemic heparin administration, but prolonged heparin administration increases the risk of bleeding. In ECMO/PCPS, unlike normal cardiotomy, ancillary circulation is often performed for several days to several weeks, during which, high-level anticoagulation and bleeding control are required. The risk of bleeding is very high during ECMO administration because platelets and clotting factors are consumed besides the heparin treatment, thus, bleeding prevention is extremely important. However, reducing the anticoagulant dose leads to the formation of thrombus, thus, controlling bleeding/coagulation is extremely important. For controlling bleeding and thrombus formation, activated partial thromboplastin time (APTT) and activated clotting time (ACT) tests are performed. In ELSO, whole blood ACT is said to be more reliable because blood cells are involved in heparin activity (Extracorporeal Life Support Organization (ELSO) Guidelines for Adult Respiratory Failure August, 2017). On the other hand, APTT is said to correlate better with heparin activity than ACT (Yoshihito Ujiie, Respiratory ECMO Manual, 2014, KOKU-SEIDO CO., LTD.). Moynihan et al. have reported that ACT showed no significant difference (p=0.177) between patients with bleeding complications of 224.5 seconds (95% confidence interval 169-304 seconds) and patients without bleeding of 229.4 seconds (180-317 seconds), while showed a significant difference (p=0.003) between patients with thrombotic complications of 224.0 seconds (178-302 seconds) and patients without thrombotic complications of 235.3 seconds (178-302 seconds). Moynihan et al. have also reported that APTT showed a significant difference (p<0.001) between patients with bleeding complications of 81.8 seconds (37-200 seconds) and patients without bleeding of 127.6 seconds (50-200 seconds), and showed a significant difference (p<0.001) between patients with thrombotic complications of 96.4 seconds (40-200 seconds) and patients without thrombotic complications of 137.3 seconds (54-200 seconds) (Moynihan K, Johnson K, Straney L, et al. Coagulation monitoring correlation with heparin dose in pediatric extracorporeal life support. Perfusion. 2017; 32(8):675-685.). Meanwhile, in a clinical study that tried to prevent bleeding and thrombus with ACT-APTT in ECMO, the incidence of bleeding complications was 69% when controlled with ACT and 80% when controlled with APTT (p=0.145), and the incidence of thrombotic complications was 41% when controlled with ACT and 39% when controlled with APTT (p=0.85), showing no difference between the two control methods, and resulting in the high incidences of the complications (Fitousis K, Klasek R, Mason P E, Masud F. Evaluation of a pharmacy managed heparin protocol for extracorporeal membrane oxygenation patients. Perfusion. 2017; 32(3):238-244.).

As such, no current method has been set as appropriate for bleeding prevention and anticoagulation therapy during ECMO administration (Esper S A, Levy J H, Waters J H, et al. Extracorporeal membrane oxygenation in the adult: a review of anticoagulation monitoring and transfusion. Anesth Analg. 2014; 118:731-743.). Thus, the most challenging complication in the ECMO/PCPS control is bleeding (Extracorporeal Life Support Organization: ELSO, https://www.elso.org/Resources/RisksandComplication-s.aspx). Brogan et al. have reported that, as a complication of ECMO, bleeding occurred in 40-60% of the patients and thrombus formation was observed in about 20% of the patients (Brogan T V, Thiagarajan R R, Rycus P T, et al. Extracorporeal membrane oxygenation in adults with severe respiratory failure: a multi-center database. Intensive Care Med. 2009; 35(12):2105-2114.). Sklar et al. have also reported that bleeding occurred in 16% and thrombus formation occurred in 53% in V-V ECMO (Sklar M C, Sy E, Lequier L, et al. Anticoagulation Practices during Venovenous Extracorporeal Membrane Oxygenation for Respiratory Failure. A Systematic Review. Ann Am Thorac Soc. 2016; 13(12):2242-2250.).

Meanwhile, von Willebrand factor (vWF) acts when platelets adhere to endovascular subcutaneous tissues and plays a central role in primary hemostasis (Sakatsume Ko et al., Acquired von Willebrand syndrome caused by high shear stress, Artificial organs, 2016; 45 (3): 225-228.). That is, vWF binds to collagen of subendothelial tissues, changes the conformational structure under shear stress to interact with platelet membrane protein GPIb complex to induce rolling of platelets on the vascular wall, and further binds to active platelet membrane proteins GPIIb/IIIa to promote platelet aggregation (Horiuchi, acquired von Willebrand syndrome associated with intractable cardiovascular disease). Also, vWF forms a complex with coagulation factor VIII to stabilize factor VIII. vWF is produced from vascular endothelial cells and bone marrow megakaryocytes, and forms a multimer by disulfide-bonding between molecules. The vWF produced from endothelial cells forms an unusually large-VWF multimer (UL-VWFM) having a molecular weight of 15 million daltons or more. However, in blood, vWF changes its molecular structure due to shear stress, and is decomposed by ADAMTS13 (a disintegrin-like and metalloproteinase with thrombospondin type 1 motifs 13) to be present as a multimer composed of 20 to 80 subunits. High-molecular-weight vWF multimers are important for primary hemostasis (Ruggeri Z M, Zimmerman T S. Variant von Willebrand's disease: characterization of two subtypes by analysis of multimeric composition of factor VIII/von Willebrand factor in plasma and platelets. J Clin Invest. 1980; 65:1318-1325.). In environments where high shear stress of blood is generated, high molecular weight vWF multimers are reduced, which may cause to develop acquired von Willebrand syndrome and exhibit a tendency of bleeding.

In ECMO, bleeding often occurs at a puncture site or the like, and acquired von Willebrand syndrome develops in all cases within 24 hours after connection (Kalbhenn J, Schmidt R, Nakamura L, et al. Early diagnosis of acquired von Willebrand Syndrome (AVWS) is elementary for clinical practice in patients treated with ECMO therapy. J Atheroscler Thromb. 2015; 22(3):265-271.). Also in the cases of wearing an implantable auxiliary artificial heart, hemorrhagic complications develop in 10-33% in which vWF is believed to be heavily involved (Draper K V, Huang R J, Gerson L B. GI bleeding in patients with continuous-flow left ventricular assist devices: a systematic review and meta-analysis. Gastrointest Endosc. 2014; 80:435-446.) (Sakatsume K, Akiyama M, Saito K, et al. Intractable Bleeding Tendency Due to Acquired Von Willebrand Syndrome After Jarvik 2000 Implant. J Artificial Organs. 2016; 9:289-292.). As such, it has been reported that vWF, which plays an important role in primary hemostasis, is affected by the mechanical occurrence of high shear stress. Thus, diagnostic methods with vWF have been studied to develop for preventing bleeding in ECMO/PCPS and auxiliary artificial heart (Hisanori Horiuchi. The AVec Study). Meanwhile, UL-VWFM produced from endothelial cells or the like forms platelet thrombus. To prevent this formation, ADAMTS13 degrades UL-VWFM and controls thrombus formation (Masanori Matsumoto, Yoshihiro Fujimura. Von Willebrand Factor Cleavage Enzyme (ADAMTS13). The Journal of the Japanese Society of Internal Medicine. 2009; 98 (7): 1586-1592.). Continued thrombus formation leads to vascular occlusion and causes ischemia of the peripheral tissue. To prevent the occlusion, high shear stress is generated when the vascular lumen narrows due to the growth of platelet thrombus, leading to structural changes of vWF to cause the degradation by ADAMTS13, which prevents vascular occlusion.

In recent years, ADAM28 has been reported as a new degradation enzyme of vWF, but the relationship with the control of thrombus formation is unknown. While ADAMTS13 only degrades vWF having the changed structure, ADAM28 also degrades vWF that has not undergone a structural change (Mochizuki S, Soejima K, Shimoda M, et al. Effect of ADAM28 on carcinoma cell metastasis by cleavage of von Willebrand factor. J Natl Cancer Inst. 2012; 104(12):906-922.). However, there are no reports that ADAM28 involves in thrombus formation.

SUMMARY OF INVENTION

Accordingly, an object of the present invention is to provide a means capable of predicting a formation of thrombus or a risk thereof in a medical device performing blood circulation by a pump, such as extracorporeal membrane oxygenation, auxiliary artificial heart, or the like, by a simple and minimally invasive method.

The present inventors have conducted intensive studies to solve the above-described problems. As a result, the relationship between thrombus formation in a medical device performing blood circulation by a pump and ADAM28 has been surprisingly revealed for the first time. Based on this finding, the present inventors have completed the present invention.

That is, according to one aspect of the present invention, there is provided a method for predicting a formation of thrombus or a risk thereof in a medical device performing blood circulation by a pump, wherein it is predicted that thrombus is formed or there is a risk thereof in the medical device when a concentration or expression amount of ADAM28 in a body fluid sample collected from a subject wearing the medical device is elevated compared with a reference value.

According to another aspect of the present invention, there is provided a method of providing data for predicting a formation of thrombus or a risk thereof in a medical device performing blood circulation by a pump, including predicting that thrombus is formed or there is a risk thereof in the medical device when a concentration or expression amount of ADAM28 in a body fluid sample collected from a subject wearing the medical device is elevated compared with a reference value.

BRIEF DESCRIPTION OF DRAWINGS

FIG. 1 is a photograph showing a thrombus attached to a centrifugal pump.

FIG. 2 is a graph showing concentration changes of von Willebrand Factor (vWF), ADAMTS13, and ADAM28.

DESCRIPTION OF EMBODIMENTS

One aspect of the present invention relates to a method for predicting a formation of thrombus or a risk thereof in a medical device performing blood circulation by a pump, wherein it is predicted that thrombus is formed or there is a risk thereof in the medical device when a concentration or expression amount of ADAM28 in a body fluid sample collected from a subject wearing the medical device is elevated compared with a reference value.

Another aspect of the present invention relates to a method of providing data for predicting a formation of thrombus or a risk thereof in a medical device performing blood circulation by a pump, including predicting that thrombus is formed or there is a risk thereof in the medical device when a concentration or expression amount of ADAM28 in a body fluid sample collected from a subject wearing the medical device is elevated compared with a reference value.

According to the present invention, a formation of thrombus or a risk thereof in a medical device performing blood circulation by a pump can be predicted by a simple and minimally invasive method.

Specifically, according to the method of one aspect of the present invention, a formation of thrombus or a risk thereof in a medical device performing blood circulation by a pump can be easily predicted. Furthermore, according to the method of one aspect of the present invention, a formation of thrombus can be detected before the blood value of vWF changes. Thus, thrombus formation can be predicted in the early stage. Furthermore, since the method requires only measuring a concentration or expression amount of ADAM28 in a body fluid sample, such a test can be performed simply. When a blood sample is used as the body fluid sample, it can be diagnosed with a portion of the blood taken by a routine blood test, and thus there is little burden on the subject. Thus, the method according to one aspect of the present invention can provide predicting and data for predicting a formation of thrombus or a risk thereof in a medical device performing blood circulation by a pump in a simple and minimally invasive manner without using expensive modalities, and can be expected to perform safe blood circulation by a pump.

Hereinafter, embodiments according to an aspect of the present invention are described, but the present invention is not limited to the following embodiments.

As used herein, the term "X to Y" indicating a range means "X or more and Y or less". Unless otherwise specified, measurements of procedures, physical properties, and the like are performed under conditions of room temperature of 20 to 25° C. and relative humidity of 40 to 50% RH.

ADAM proteins (ADAMs: disintegrin and metalloproteinases) are multifunctional proteins involved in ectodomain shedding of transmembrane proteins, and cell adhesion and infiltration (Edwards D R, Handsley M M, Pennington C J. The ADAM Metalloproteinases. Mol Aspects Med. 2008; 29(5):258-289.)(Murphy G. Regulation of the proteolytic disintegrin metalloproteinases, the 'Sheddases'. Semin Cell Dev Biol. 2009; 20(2):138-145.). The human genome contains 25 ADAMs including 4 pseudo-genes, and 21 ADAMs are composed of 13 proteolytic ADAMs having proteolytic activity and 8 non-proteolytic ADAMs (Edwards D R, Handsley M M, Pennington C J. The ADAM Metalloproteinases. Mol Aspects Med. 2008; 29(5):258-289.) (Shiomi T, Lemaitre V, D'Armiento J, Okada Y. Matrix metalloproteinases, a disintegrin and metalloproteinases, and a disintegrin and metalloproteinases with thrombospondin motifs in non-neoplastic diseases. Pathol Int. 2010; 60(7):477-496.). Proteolytic ADAMs share the metalloproteinase domain of matrix metalloproteinases (MMPs), and typical proteolytic ADAMs include propeptide, metalloproteinase, disintegrin-like, cysteine-rich, epidermal growth factor-like, transmembrane and intracellular domains. Many proteolytic ADAMs, including ADAMS, ADAMS, ADAM12, ADAM15, ADAM17, ADAM19, and ADAM28, are overexpressed in human cancers and known to be associated with cancer proliferation and progression. However, it has not been suggested to date that ADAM28 can be a useful indicator for predicting a formation of thrombus or a risk thereof in a medical device performing blood circulation by a pump.

ADAM28 is a known protein, and the amino acid sequence and cDNA sequence thereof are also known. There are two types of ADAM28: a membrane type (ADAM28m) and a secretory type (ADAM28s). Representative amino acid sequence and cDNA sequences of human membrane-type ADAM28 (and mature forms thereof) and representative amino acid sequence and cDNA sequences of human secretory-type ADAM28 (and mature forms thereof) are disclosed in WO2016/143702. Note that the "human membrane-type ADAM28" means that the amino acid sequence or nucleotide sequence of membrane-type ADAM28 has an amino acid sequence or nucleotide sequence identical or substantially identical to the amino acid sequence or nucleotide sequence of membrane-type ADAM28 naturally expressed in humans. The "substantially identical" means that the amino acid sequence or nucleotide sequence of interest has 70% or more (preferably 80% or more, more preferably 90% or more, further preferably 95% or more, most preferably 99% or more) identity to the amino acid sequence or nucleotide sequence of the membrane-type ADAM28 naturally expressed in humans and has the function of the human membrane-type ADAM28. The same applies to non-human biological species and proteins other than membrane-type ADAM28, genes, and fragments thereof.

In the method according to the present invention, the concentration or expression amount of ADAM28 in a body fluid sample obtained from a subject is measured for use as a marker. Further in a preferred embodiment, the concentration or expression amount of vWF and/or ADAMTS13, in addition to ADAM28, is measured for use as a marker. This can further increase the accuracy of predicting a formation of blood vessel or a risk thereof.

vWF is a plasma protein that plays an important role in blood coagulation. vWF is mainly produced in vascular endothelium and released into blood in the form of high molecular weight multimers. Wild-type human vWF is a polypeptide composed of a total of 2813 amino acids including the signal peptide and the pro-region thereof. The amino acid sequences of the wild-type human vWF and the amino acid sequences of the wild-type human mature vWF subunits are disclosed in WO2004/035778.

ADAMTS13 is a known protein, and the amino acid sequence and the cDNA sequence thereof are also known. ADAMTS13 is a zinc-based metalloproteinase belonging to the ADAMTS family, and is believed to reduce the multimer size of vWF and control the function of vWF by specifically cleaving the binding of Tyr1605 and Met1606 in vWF. Details of the structure and sequence information for human ADAMTS13 are disclosed in Zheng X et al., J Biol Chem. 2001; 276 (44): 41059-63.

As used herein, the "medical device performing blood circulation by a pump" includes an artificial lung (e.g., extracorporeal membrane oxygenation), an auxiliary artificial heart, and the like.

As used herein, the "subject" is a subject, preferably a human subject, who needs a treatment with a medical device performing blood circulation by a pump.

As used herein, the "body fluid sample" is any body fluid from a living body (organism) in which a measurement of the concentration or expression amount of ADAM28, and optionally the concentration or expression amount of vWF and/or ADAMTS13, can be performed. The body fluid sample is preferably a blood sample. The blood sample may be whole blood, plasma, or serum. As the blood sample, the blood (whole blood) collected from a subject may be used as is, or a sample supplemented with an additive, such as EDTA potassium salt, heparin, sodium citrate for the purpose of preventing coagulation or the like may be used. The timing for collecting a body fluid sample from a subject is not particularly limited. When the body fluid sample is a blood sample, the blood sample may be arterial blood or venous blood.

The body fluid sample used in the method according to the present invention is preferably used for measurement immediately after collected from a subject, but may be used for measurement after storage. For example, the storage method of the blood sample is not particularly limited as long as the value of the marker in the sample is not changed. For example, it is preferred that the sample be preserved at low temperatures without freezing, such as 0-10° C., and in the long-term storage, it is preferred that the sample be cryopreserved at −80° C. or in liquid nitrogen.

In the method according to the present invention, the measurement of the value of the marker can be performed using conventionally known methods described below.

As used herein, the "expression amount" of a protein is intended to include both the expression of an RNA (transcription product) that is complementary to a gene encoding the protein and the expression of the protein (translation product) itself. Thus, as used herein, the expression amount of the protein refers to the expression amount or expression intensity of the transcription product or translation product. The expression amount can usually be analyzed by the production amount of the transcription product, or the production amount, activity, or the like of the translation product. The "concentration" of a protein also means the abundance (expression amount) of the protein per unit volume of a body fluid sample (e.g., a blood sample).

The expression amount of a protein may be measured by measuring a transcription product of a gene encoding the protein, that is, mRNA or by measuring a translation product from the gene, that is, the protein itself. Preferably, the measurement is performed by measuring a translation product of the gene. Note that the transcription product of the gene includes cDNA obtained by reverse transcription from mRNA.

Measurement of expression amount of the translation product can be performed by quantifying the translated protein or measuring the activity of the protein. Examples of the quantification method of the protein include an electrophoresis method, a Western blotting method, or a chromatography method using affinity chromatography, ion-exchange chromatography, gel filtration chromatography, reverse phase chromatography, immunochromatography, and the like, or a method for measuring mass spectrum. The measurement can be performed simply and accurately by using an antibody specific to the protein.

The antibody can be produced by known methods. Alternatively, the antibody is available from, for example, MyBioSource, Inc., Invitrogen, Santa Cruz Biotechnology, Inc., Sigma-Aldrich Co. LLC, or the like, and can be obtained and used as appropriate. The antibody for detection may be a polyclonal antibody or monoclonal antibody.

Detection of the protein using an antibody can be performed by, but is not limited to, an immunochromatography method, a Western blotting method, an EIA method, an ELISA method, an RIA method, a flow cytometry method, or the like. The antibody can be labeled by a fluorescence label, a radioactive label, an enzyme, biotin, or the like, and a secondary antibody for detection labeled as such can be used. Currently, in clinical practice, the presence of myocardial injury is assessed by detecting myocardial troponin T in blood samples by immunochromatography method (Trop T Sensitive, Roche Diagnostics K.K.). Thus, similarly in the method according to the present invention, by measuring markers such as ADAM28 by immunochromatography method, it is expected that a measurement method useful for predicting a formation thrombus or a risk thereof in a medical device performing blood circulation by a pump, which is clinically minimally invasive and allows simple measuring, which can be universalized at a low cost, which is highly accurate and reproducible, and which is capable of standardizing the measurements or the like, is established. Further, as a result, it is expected that appropriate treatment can be administered, and hemolysis and thrombus formation can be controlled. Note that the above measurement by an immunochromatography method is preferably performed with an immunochromatography test strip. It is preferred that the immunochromatography test strip has a sample pad region that receives a blood sample, a conjugate pad region containing a labeled antibody capable of binding to an indicator substance such as ADAM28, a membrane body on which a specimen is deployed, and a test line in which an antibody capable of binding to the indicator substance is fixed on the membrane body and the antibody is allowed to bind to the indicator substance bound by the labeled antibody in the conjugate pad region. Furthermore, it is more preferred that the immunochromatographic test strip has a control line that can determine the amount of labels bound in the test line described above. Note that it is further preferred that the labels are those that develop stronger color depending on the concentration.

The expression amount of the transcription product may be measured, for example, by using a nucleotide containing whole or a portion of a nucleotide sequence of an mRNA as a probe or a primer to measure the extent of gene expression in a sample. For example, the expression amount can be measured, by a method using a microarray (microchip), a Northern blot method, a quantitative PCR method, or the like. As the quantitative PCR method, an agarose gel electrophoresis method, a polyacrylamide gel electrophoresis method, a fluorescence probe method, an RT-PCR method, a real-time PCR method, an ATAC-PCR method, a Taqman PCR method, a SYVER (registered trademark) green method, a Body Map method, a serial analysis of gene expression (SAGE) method, and a micro-analysis of gene expression (MAGE) method are known, and these methods can be appropriately used. Next-generation sequencers may also be used for evaluation. These methods can be used to measure the amount of mRNA with a nucleotide probe or primer that hybridizes to the mRNA. The nucleotide length of the probe or primer used for the measurement is preferably 10 to 50 mers, more preferably 15 to 25 mers.

When simultaneously measuring expressions of multiple genes, particularly expressions of genes of several types, it is preferable to use a DNA microarray. A DNA microarray can be produced by fixing nucleotides consisting of a nucleotide sequence of the gene or containing a portion thereof on an appropriate substrate. Examples of the substrate for fixing include a glass plate, a quartz plate, and a silicon wafer. Examples of the size of the substrate include 3.5 mm×5.5 mm, 18 mm×18 mm, and 22 mm×75 mm, but it can be variously set depending on the number of spots of the probe and the size of the spots on the substrate. Examples of the method for fixing a polynucleotide or fragment thereof include a method of electrostatically coupling the nucleotide using the charge onto a solid phase support which is surface-treated with a polycation such as polylysine, polyethyleneimine, or polyalkylamine, and, a method of covalently bonding a nucleotide in which a functional group such as an amino group, an aldehyde group, a thiol group, or biotin is introduced to a solid phase surface in which a functional group such as an amino group, an aldehyde group, or an epoxy group is introduced. Immobilization may be performed using an array machine. The type and amount of mRNA can be determined by immobilizing at least one gene or a fragment thereof to a substrate to prepare a DNA microarray, contacting a subject-derived mRNA or cDNA labeled with a fluorophore with the DNA microarray to make hybridization, and measuring the fluorescence intensity on the DNA microarray.

In the method according to the present invention, the concentration or expression amount of ADAM28 measured by the method described above may be compared with a reference value to predict a formation of thrombus or a risk thereof in a medical device performing blood circulation by a pump. That is, a method of predicting a formation of thrombus or a risk thereof in a medical device performing blood circulation by a pump is disclosed herein. Also disclosed herein is a method of providing data for predicting a formation of thrombus or a risk thereof in a medical device performing blood circulation by a pump. In the methods, as described above, when a concentration or expression amount of ADAM28 is elevated compared with a reference value, it is predicted that thrombus is formed or there is a risk thereof in the medical device performing blood circulation by a pump.

When the concentration or expression amount of vWF and/or ADAMTS13, in addition to ADAM28, is further used in combination as a marker, the accuracy of the prediction based on ADAM28 can be improved by comparing the value of the marker measured by the above-described method to a reference value.

As used herein, the "reference value" is a numerical value that may serve as a reference for determining an elevation or reduction in the expression amount or concentration in the method according to the present invention. Examples of the reference value include a measured value of the concentration or expression amount of ADAM28 in a body fluid sample collected from a person having no observed thrombus formation (e.g., a healthy subject, a subject before blood circulation by a pump, or a subject who is not expected to have thrombus formation except one immediately after surgery). The reference value is preferably a measured value of the concentration or expression amount of ADAM28 in a body fluid sample collected from a healthy subject or a subject before blood circulation by a pump. The same applies to when the concentration or expression amount of vWF and/or ADAMTS13, in addition to ADAM28, is further used in combination as a marker.

The value of the marker measured in the past in the same subject may also be used as a reference value.

Since the value of the marker may vary depending on the measurement method, the reference value must be set in each measurement method.

According to yet another aspect of the present invention, a detection reagent for use in the method according to one embodiment of the present invention described above is provided. Also, a kit for use in the method according to one embodiment of the present invention described above, including the detection reagent, is provided. The detection reagent is one that enables the detection of the concentration or expression amount of ADAM28, optionally vWF and/or ADAMTS13, in the body fluid sample described above. Examples of such a detection reagent include an antibody for specific binding to a protein (e.g., ADAM28) in a body fluid sample, and a DNA or RNA or oligonucleotide for hybridization to an mRNA of a protein gene (e.g., an ADAM28 gene) in a body fluid sample. Such a DNA or RNA may be a probe capable of detecting hybridization using a fluorescent label or the like. Alternatively, the DNA or RNA may be a primer that can be used to amplify an mRNA. The kit can include, in addition to the detection reagent described above, other reagents required for detection, such as a buffering agent, various nucleotides, and other reagents required for hybridization or antibody binding.

EXAMPLES

The effects of the present invention will be described using the following Examples and Comparative Examples, but the technical scope of the present invention is not limited to the following Examples.

[Creation of Animal Model]

In the experiment, sheep (female, 5 years old) were subjected to the test after a seven-day quarantine and conditioning period.

The right jugular vein was cannulated for blood delivery, and an extracorporeal circulation device composed of a centrifugal pump was connected to the opposite end. Blood removal was performed via cannulation to the right jugular vein. Blood circulation conditions by the centrifugal pump were at 0.7 to 1.6 L/min, and anticoagulation control was performed with heparin.

The experiments were conducted in accordance with the guidelines for animal experiments by Terumo Corporation.

[Blood Collection]

Blood was collected from the external jugular vein with an EDTA blood collection tube, and centrifuged at 3000 rpm for 10 minutes, and plasma was collected. The plasma was stored at $-20°$ C. and then subjected to vWF, ADAMTS13, and ADAM28 measurements.

[Confirmation of Thrombus Formation]

Thrombus attached to the centrifugal pump of the extracorporeal circulation device was visually confirmed (FIG. 1).

[Measurement of Von Willebrand Factor (vWF) Concentration]

The concentration of vWF in the plasma was measured using Sheep von Willebrand Factor (vWF) Elisa kit (Competitive ELISA) (MyBioSource, Inc.) according to the attached manual.

The absorbance measurement in the ELISA analysis was performed by repeatedly measuring three times with a precision-controlled microplate reader (MICROPLATE READER SH9000, CORONA ELECTRIC Co., Ltd.), and the average value was used as the final data.

[Measurement of ADAMTS13 Concentration]

The concentration of ADAMTS13 in the plasma was measured using Sheep Von Willebrand Factor cleaving protease (vWF-cp), ELISA Kit (MyBioSource, Inc.) according to the attached manual.

The absorbance measurement in the ELISA analysis was performed by repeatedly measuring three times with a precision-controlled microplate reader (MICROPLATE READER SH9000, CORONA ELECTRIC Co., Ltd.), and the average value was used as the final data.

[Measurement of ADAM28 Concentration]

The concentration of ADAM28 in the plasma was measured using Sheep A Disintegrin and Metalloprotease 28 (ADAM28) ELISA Kit (MyBioSource, Inc.) according to the attached manual. The absorbance measurement in the ELISA analysis was performed by repeatedly measuring three times with a precision-controlled microplate reader (MICROPLATE READER SH9000, CORONA ELECTRIC Co., Ltd.), and the average value was used as the final data.

The results are shown in FIG. 2. In FIG. 2, the day on which thrombus formation was confirmed is displayed as Day 0.

As shown in FIG. 2, the concentration of ADAM28 was first elevated, followed by elevation of the concentrations of vWF and ADAMTS13, in this order. Then, thrombus formation was confirmed. From the above, it can be seen that thrombus formation can be predicted in the earlier stage by using ADAM28 as an indicator than using vWF or ADAMTS13 as an indicator.

This application is based on Japanese Patent Application No. 2020-044275 filed on Mar. 13, 2020, the disclosure of which is incorporated herein by reference in its entirety.

The invention claimed is:

1. A method for reducing thrombus formation in a patient requiring insertion of a medical device into the patient to perform blood circulation, the method comprising:

measuring a concentration or amount of ADAM28 in a
  first fluid body sample collected from the patient before
  the medical device is inserted into the patient;

inserting the medical device into the patient;

collecting a second fluid body sample from the patient after the inserting of the medical device into the patient;

measuring a concentration or amount of ADAM28 in the
  collected second fluid body sample from the patient;
  and when the concentration or amount of ADAM28 in the
collected second fluid body sample from the patient is
  higher than the concentration or amount of ADAM28 in
  the first fluid body sample collected from the patient
  before the inserting of the medical device, administer-
  ing an anticoagulation treatment to the patient to reduce
thrombus formation during use of the medical device.

2. The method according to claim 1, wherein the first fluid
body sample collected from the patient is a blood sample.

3. The method according to claim 1, wherein the concen-
tration or amount of ADAM28 in the second fluid body
sample collected from the patient after the inserting of the
medical device into the patient is measured with a detection
reagent that detects a concentration or expression amount of
ADAM28.

4. The method according to claim 3, wherein the detection
reagent is an antibody against ADAM28 or a DNA or RNA
or oligonucleotide for hybridization to an mRNA of
ADAM28 gene.

\* \* \* \* \*